United States Patent [19]

Luther

[11] Patent Number: 5,098,394
[45] Date of Patent: Mar. 24, 1992

[54] BIASED SHUT OFF VALVE ASSEMBLY FOR NEEDLE AND CATHETER

[76] Inventor: Ronald B. Luther, 530 Kings Rd., Newport Beach, Calif. 92663

[21] Appl. No.: 531,348

[22] Filed: May 31, 1990

[51] Int. Cl.⁵ .............................................. A61M 5/18
[52] U.S. Cl. .................................... 604/167; 604/169
[58] Field of Search ............... 604/167, 169, 237, 246, 604/256, 905

[56] References Cited

U.S. PATENT DOCUMENTS

| | | | |
|---|---|---|---|
| 3,895,632 | 7/1975 | Plowiecki | 604/169 |
| 4,240,411 | 12/1980 | Hosono | 604/167 |
| 4,874,377 | 10/1989 | Newgard et al. | 604/256 |
| 4,917,668 | 4/1990 | Haindl | 604/169 |
| 4,943,280 | 7/1990 | Lander | 604/169 |
| 4,960,412 | 10/1990 | Fink | 604/256 |

FOREIGN PATENT DOCUMENTS 2034185  6/1980  United Kingdom .

Primary Examiner—John J. Wilson
Assistant Examiner—Michael Lynch
Attorney, Agent, or Firm—Willie Krawitz

[57] ABSTRACT

An assembly of a hub, biased valve and catheter is provided for insertion therethrough with a hub and attached needle. The hub, valve and catheter assembly defines an exit bore which is sealed at its entrance by the valve when biased into its normally closed position. When the needle is inserted into the hub assembly, it will contact and unseat the closed, biased valve. After the needle unseats the valve, it will enter and seal the exit bore and then engage the catheter. The needle and catheter portion of the assembly are then inserted into a patient. The needle is then withdrawn and discarded, and the catheter portion of the assembly will remain in place in the patient. As the needle is withdrawn back along the exit bore, it will move out of contact with the valve. This enables the valve to be biased back into its closed position against the entrance of the exit bore, thereby sealing the hub, valve and catheter assembly against blood flashback. To administer a solution to the patient, a connection is made from a fluid line through the assembly. The fluid line and associated luer and/or hub will similarly unseat the valve and enter and seal the exit bore of the hub with minimal loss of blood. The hub, valve and catheter assembly thereby reduces the possiblity of infection from the patient's blood.

5 Claims, 1 Drawing Sheet

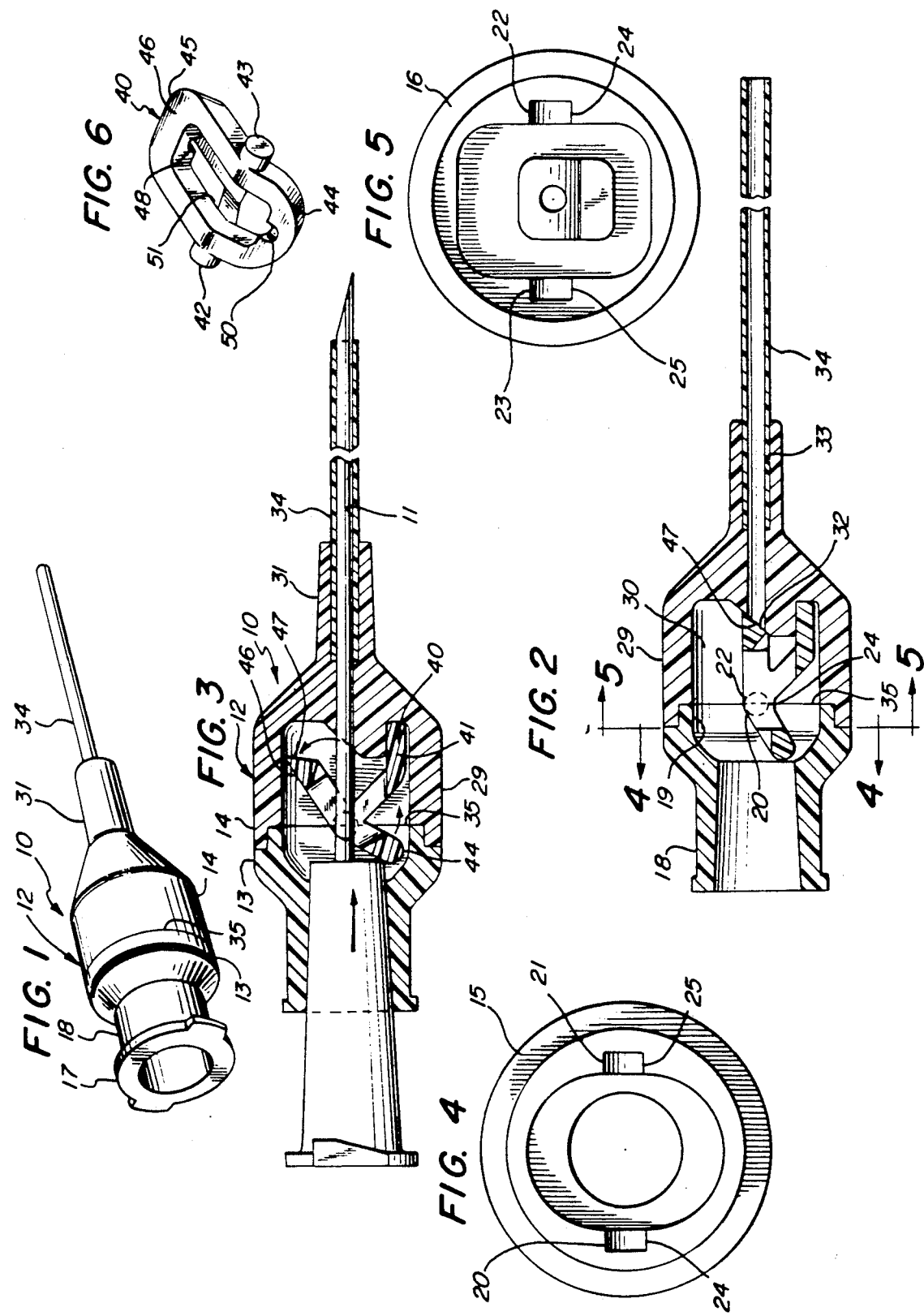

BIASED SHUT OFF VALVE ASSEMBLY FOR NEEDLE AND CATHETER

BACKGROUND OF THE INVENTION

This invention relates to a new and improved hub, valve and catheter assembly for penetration into a vein along with a needle which is inserted separately into the assembly. Following retraction of the needle from the patient, the catheter remains in place in the patient as part of the hub, valve and catheter assembly, and the needle is then withdrawn, and discarded. The same connection is then made between a liquid line and the assembly, followed by administration of solution. This procedure is accomplished with a reduced loss of blood due to flashback.

Usually, insertion and withdrawal of a needle from an assembly of this general type is accompanied by blood flashback, and when a liquid connection is subsequently made such as with and I.V. line, blood flashback will also occur. Normally, the loss of blood due to flashback would not be a significant problem, however with the AIDS epidemic, and with other types of highly contagious diseases prevalent such as hepatitis, it becomes extremely important that blood contamination be maintained at an absolute minimum.

Conventional devices of the present type employing flexible valves or diaphragms either do not reduce blood flashback, or do not operate uniformly.

It would be desirable to provide a device which would reduce blood flashback, and which functions uniformly for this purpose during insertion of a needle into and withdrawal from both the patient and the device. Similarly, when a liquid supply system such as an I.V. system is repeatedly connected and disconnected to the patient, blood flashback should be reduced. Also, it would be desirable that the device provide uniform performance characteristics during use, while maintaining reasonable sterility.

THE INVENTION

According to the invention, an improved hub, valve and catheter assembly is provided for reducing blood flashback, comprising a hub portion having an exit bore and a catheter bonded into or attached to the exit bore. A biased valve is mounted at the entrance to the exit bore, and in its normally biased position, the valve closes off the entrance, and seals the bore.

When a needle or stylet is inserted through the hub and into the entrance of the exit bore, it will contact and unseat the valve at the entrance, and then seal off the exit bore as it passes therethrough. Further movement through the exit bore will position the needle or stylet within the catheter, and the needle and catheter are then inserted into a patient.

Following insertion, the needle is withdrawn and discarded, leaving the catheter in place in the patient, while still being attached to and forming part of the hub, valve and catheter assembly. As the needle is removed from the patient and withdrawn back out the exit bore, it will move out of contact and release the valve, thereby permitting the valve to be biased closed again while maintaining the exit bore sealed off.

Hence, the amount of blood flashback escaping from the device will be greatly reduced. Following placement of the catheter in the patient, a liquid line is inserted into the hub, valve and catheter assembly, and liquid medication is fed through the line and the hub assembly for administration to the patient. The amount of blood escaping due to flashback will similarly be minimized, even for repeated administrations of the liquid medication.

BRIEF DESCRIPTION OF THE DRAWINGS

FIG. 1 is an external perspective view of the assembly of a hub, biased valve and catheter of this invention;

FIG. 2 is an axial view of the assembly in sectional side elevation showing the valve in a closed position;

FIG. 3 is an axial view of the assembly in sectional side elevation showing a needle inserted therein, the valve being biased open by the needle;

FIG. 4 is a sectional view taken along the lines 4—4 of FIG. 2;

FIG. 5 is a sectional view taken along the lines 5—5 of FIG. 2; and,

FIG. 6 is an external perspective view of the on-off biased valve shown in FIGS. 2 and 3.

DESCRIPTION OF THE PREFERRED EMBODIMENTS

The hub, valve and catheter assembly 10 of this invention is shown in FIGS. 2, 3 and 6, with a needle 11, defining a bevel area 11a, or other similar device such as a stylet mounted into the assembly 10, for insertion into a patient. The assembly 10 comprises a hub structure 12, having a distal portion 13 and a proximal portion 14 which are sealed along mating edges 15 and 16 to form the hub. As shown in FIG. 2, the distal portion 13 provides a luer lock 17 at the end of a tubular portion 18, and the luer lock and tubular portion will enable the assembly to engage a needle holder or a hub attached to a liquid line; this will be discussed, infra. The tubular portion 18 tapers outwardly to form an enlarged opening 19 circumscribed by the mating edge 15. Semi-circular cut-outs 20 and 21 are formed on mating edge 15, and when the distal and proximal portions 13 and 14 are joined together, similarly configured cut-outs 22 and 23 on the mating edge 16 of proximal portion 14 will oppose the cut-outs 20 and 21 and form trunnion cavities 24 and 25. The proximal portion 14 is shown in FIG. 3, and comprises a barrel-shaped portion 29, which together with the enlarged opening 19 of distal end 13, will form a hollow interior 30 when the distal and proximal portions 13 and 14 are bonded together. The barrel-shaped portion 29 tapers downwardly to form a tubular portion 31 which defines a rear entrance 32, and a forward bore 33 into which a catheter 34 is bonded or press fitted.

Mating edges 15 and 16 are joined by adhesive bonding, heat sealing, ultrasonic bonding, etc., to form a circumferential joining line 35 when the distal and proximal portions 13, 14 are joined to produce the hub structure 12. The assembly is about one 1 inch long and about three-eighths (⅜) inches in diameter at the barrel portion 29.

The valve 40 which seals off the entrance 32 to the tubular portion 31 is shown in FIGS. 2, 3 and 6, and is typically constructed of a plastic material suitable for valve use. Suitable plastics are injection molded nylon, acetal resins such as polyoxymethylene homopolymers sold as DELRIN, etc.

The valve 40 has an integrally formed spring base 41 which rests on the bottom of the barrel-shaped portion 29, and the valve rotates around trunnions 42 and 43 mounted in the trunnion cavities 24 and 25 of the hub structure 12. In the closed position, the valve is compressed between the trunnion cavities and the spring base 41 which bears against the bottom of hollow interior 30 of hub structure 12.

The valve 40 is initially assembled into place by mounting the trunnions 42 and 43 onto the semi-circular cutouts 21 and 22 of proximal portion 14, followed by bonding the distal and proximal portions together. This bonding step will bring the semi-circular cut-outs 21 and 21, 22 and 23 into coincidence to form the trunnion cavities 24 and 25 into which the trunnions 42 and 43 of the valve will rotate. The bonding step will also form the hub structure 12, with the valve 40 mounted inside; the catheter is mounted or bonded into the hub prior to assembly.

The rearward part 44 of the valve is bent downwardly (about 30°) to provide sufficient clearance for the needle 11 to move over and through the valve as it passes into and along tubular portion 31.

The forward end 45 of the valve 40 rotates between an open and a closed position to open or seal off the rear entrance 32 of the tubular portion 31. The forward end 45 defines an outer rim area 46 having an upwardly sloping, leading face 47 which fits against and seals the entrance 32 of the tubular portion 31 when the valve is biased upwardly by the spring base 41. The lower part of the leading face 47 defines a semi-circular slot 48. A central groove 50 is formed aligned with a longitudinal, central slot 51 in the interior part of the valve, and slot 48. When the needle 11 moves through the hub and along the valve, it will pass along and be aligned by the central groove 50 and slot 51. When the needle tip 11a enters the slot 48, it will lift up the leading face 47 to unseat the valve from entrance 32 as the needle enters the tubular portion 31; the unseated valve is shown in FIG. 3.

As the needle moves through the tubular portion 31, it seals the tubular portion 31, and then frictionally engages the catheter 34. The assembled needle and catheter are then ready for insertion into the patient. When the needle is removed from the patient, it is withdrawn along the tubular portion 31 and moves out of contact with the valve. This will release the valve which is then biased closed; hence, any blood flashback accompanying removal of the needle will be reduced considerably.

In a similar manner, insertion or withdrawal of a liquid line assembly from the hub, valve and catheter assembly 10 of this invention will again unseat or reseat the valve and enable liquid from an I.V. or similar line to be fed to a patient, while minimizing problems due to blood flashback.

Obviously, other types of valves may be employed besides the valve 40 which is illustrated. For example, separate spring biasing may be used instead of an integrally formed biasing to rotate the valve. Also, a spring biased or integrally biased vertically movable valve may be employed rather than a rotatably movable valve to seal off the rear entrance 32 to the tubular portion 31.

It will be appreciated that the biased valve of this invention can be employed for purposes other than preventing or passing liquid through the hub, valve and catheter assembly. For example, medical components such as luer hubs (without an attached needle), medical instruments, wire inserters, and so forth may be passed through the assembly.

I claim:

1. A hub, valve and catheter assembly for providing a reduced amount of blood loss due to blood flashback, comprising:
   a.) a hub element providing an entrance opening, an exit bore defining the entrance opening, and a catheter mounted within the exit bore; and,
   b.) a biased, deformable valve rotatably mounted about trunnions within the hub element, the valve defining a peripheral, reinforcing rim including a forward rim portion having an upper leading edge and a lower wedge portion biased against rotation by engagement with the hub, the reinforcing rim providing a trailing portion including a rearward trailing edge downwardly offset from the forward rim portion, and aligned notches defined by the upper leading edge and the rearwardly trailing edge, the valve in a normally biased position being rotatable about the trunnions, to close off and seal the entrance opening to the exit bore along the upper leading edge of the forward rim portion, and in an open position being adapted for rotational biasing about the trunnions to become unseated from and thereby unseal the entrance opening; whereby:
   i. medical components are adapted for insertion through the entrance opening of the hub assembly and through the aligned notches of the valve and into the entrance opening of the exit bore, thereby deformably unseating the valve and unsealing the entrance to the exit bore; and,
   ii. the medical components are adapted for movement along the exit bore in sealing relationship therewith, for movement through the catheter, for insertion into a patient along with the catheter and for withdrawal from the patient leaving the catheter in place in the patient, thereby minimizing the escape of blood due to flashback.

2. The assembly of claim 1, in which the valve is constructed of an injection molded plastic material.

3. A hub, valve and catheter assembly for providing a reduced amount of blood loss due to blood flashback, comprising:
   a.) a hub element providing an entrance opening, an exit bore defining the entrance opening, and a catheter mounted within the exit bore; and,
   b.) a biased, deformable valve rotatably mounted about trunnions within the hub element, the valve defining a peripheral, reinforcing rim including a forward rim portion having an upper leading edge and a lower wedge portion biased against rotation by engagement with the hub, the reinforcing rim providing a trailing portion including a rearward trailing edge downwardly offset from the forward rim portion, and aligned notches defined by the upper leading edge and the rearwardly trailing edge, the valve in a normally biased position being rotatable about the trunnions, to close off and seal the entrance opening to the exit bore along the upper leading edge of the forward rim portion, and in an open position being adapted for rotational biasing about the trunnions to become deformably unseated from and thereby unseal the entrance opening; whereby:
   i. an assembly of a mounted needle is adapted for insertion through the entrance opening of the hub assembly and through the aligned notches of the valve into the entrance opening of the exit bore. thereby deformably unseating the valve and unsealing the entrance to the exit bore:

ii. the mounted needle is adapted for movement along the exit bore in sealing relationship therewith. for movement through the catheter. for insertion into a patient along with the catheter and for withdrawal from the patient leaving the catheter in place in the patient:

iii. upon withdrawal of the needle out of the exit bore, the mounted needle moves out of contact with the valve, and the valve is biased into a sealing relationship with the opening to the exit bore. thereby minimizing the escape of blood from the patient due to flashback; and iv. connection of the hub, valve and catheter assembly to an I.V. supply system is similarly accomplished. thereby minimizing the escape of blood due to flashback.

4. The assembly of claim 3, including a luer lock and liquid supply system connected to the assembly.

5. The assembly of claim 3, in which the valve is constructed of an injection molded plastic material.

* * * * *